United States Patent [19]

James et al.

[11] Patent Number: 5,039,219

[45] Date of Patent: Aug. 13, 1991

[54] LUMINESCENCE SYSTEM AND METHOD FOR DETERMINING THE NATURE OF SUBSTANCES BY MEASURING FLUORESCENCE AND PHOSPHORESCENCE PROPERTIES

[75] Inventors: Douglas R. James; William R. Ware, both of London, Canada

[73] Assignee: Photon Technology, South Brunswick, N.J.

[21] Appl. No.: 357,118

[22] Filed: May 26, 1989

[51] Int. Cl.$^5$ ............................................. G01N 21/64
[52] U.S. Cl. ................................. 356/318; 250/458.1
[58] Field of Search ............................. 356/317, 318; 250/458.1, 459.1, 461.1

[56] References Cited

U.S. PATENT DOCUMENTS

| 3,975,098 | 8/1976 | West ........................................ 356/318 |
| 4,198,567 | 4/1980 | Eneroth et al. ................... 356/318 X |
| 4,877,965 | 10/1989 | Dandliker et al. ............... 356/318 X |
| 4,895,156 | 1/1990 | Schulze ......................... 250/458.1 X |

OTHER PUBLICATIONS

Braumik et al. "Stroboscopic Time-Resolved Spectroscopy", Rev. Sci. Inst., vol. 36, #1, Jan. 65, pp. 37-40.
Bennett, Instrument to Measure Fluorescence Lifetimes in the Millimicrosecond Region. Rev. Sci. Inst., vol. 31, #12, Dec. 1960, pp. 1275-1279.
Tuan et al., High Resolution Luminescence Spectrometer Applied Optics, vol. 12, #6, Jun. 1973, pp. 1286-1292.
Strambini et al., A Flash Apparatus for Time-Dependent Phosphorescence Measurements, A Spectroscopic Aid, Canadian Jour. of Spectroscopy, vol. 21, #1, Jan.-Feb. 1976, pp. 1-5.

Primary Examiner—Vincent P. McGraw
Attorney, Agent, or Firm—John D. Kaufmann

[57] ABSTRACT

Disclosed is an integrated, multi-module luminescence measuring system. The system can selectively conduct lifetime decay or steady-state measurements of light emitted by a sample which receives exitation light. The system includes: a sample chamber which directs monochromatized, focused excitation light from a selected source at a selected sample and directs any resultant emitted light through a monochromator to either a first gated photodetector or a second regular photodetector. Also present is a reference module with a regular photodetector which may selectively receive a portion of the excitation light. A lifetime decay detector module pulses a selected light source and the gated photodetector so that a converter produces digital signals related to output signals from the photodetector, the digital signals representing the integral of the intensity of the emitted light over a selected time. A steady-state detector module pulses a selected light source and includes a resettable integrator-A/D converter combination which receives the output from the regular photodetectors and produces digital signals representing the integrals over varying time intervals of such outputs. The integrator is reset and the A/D convertor is turned on whenever the light source is pulsed. A data processing module controls sample selection, the wavelengths of the excitation and emitted lights, light source selection, the number and time-width of the various integrations, and the storage and processing of the resulting digital signals.

3 Claims, 6 Drawing Sheets 5,039,219

LUMINESCENCE SYSTEM AND METHOD FOR DETERMINING THE NATURE OF SUBSTANCES BY MEASURING FLUORESCENCE AND PHOSPHORESCENCE PROPERTIES

BACKGROUND OF THE INVENTION

The present invention relates to luminescence systems and methods, and more particularly relates to instruments and methods for the chemical analysis of substances by the measurement of fluorescence and phosphorescence emission properties.

The chemical analysis of luminescent substances with instruments that employ light to excite samples of such substances and measure light emissions therefrom has become an essential tool in a variety of fields. For example, in the fields of health care, environmental science and industrial process control, to name a few, fluorometric chemical analysis of luminescent substances is being employed primarily because of its sensitivity and selectivity.

In general, luminescence analysis involves a process in which a sample, exposed to radiation of one wavelength, absorbs this radiation and reemits radiation of the same or a longer wavelength.

Luminescence is the emission of visible or invisible radiation unaccompanied by high temperature by any substance as a result of absorbtion of exciting energy in the form of photons. It is a general term which includes both fluorescence and phosphorescence. A fluorescence lifetime is the characteristic time it takes for a fraction of the excitation energy contained in a molecule to be re-emitted as light. The characteristic fraction is 1/e of the initial excitation intensity. In the present invention, if this re-emission occurs after about $10^{-8}$ seconds, it is called fluorescence. Reemission after about $10^{-6}$ seconds or more is called phosphorescence. The re-emissions are used to determine the material which is the source of the fluorescence or phosphorescence. This basic process has virtually become an essential analytical tool in many fields because of the superb sensitivity that it offers over other systems. For example, with spectrophotometers, detecting micromolar concentrations is a major task. With luminescence type measurements, detecting picomolar concentrations is routine. Luminescence measurements can reveal much more than just concentration They can detect structural changes and orientation as well by means of lifetime measurements and other related measurements.

Determining the fluorescence lifetime of a compound is the most exacting of the measurements of fluorescence properties. This is primarily due to the forementioned extremely brief time period of the emission, typically $10^{-12}$ to $10^{-8}$ seconds. Of necessity therefore, prior instruments for determining fluorescence lifetimes have been complex, expensive and difficult to use.

Although such systems have been used successfully, they have generally been accepted as a routine tool in only the most sophisticated installations primarily because of cost, structural and operational complexity, and difficulty in interpreting results. Attempts to produce systems that are relatively simple and less expensive have often resulted in systems of greatly reduced precision. As such, those concerned with the development of systems that measure fluorescence and phosphorescence emission lifetime properties have recognized the need for a simple, inexpensive automated system that maintains at least the same high precision of prior art systems. The present invention fulfills this need

SUMMARY OF THE INVENTION

It is an object of the present invention to provide a reliable luminescence system that is easy to use.

Another object of the invention is the provision of a relatively low-cost system that has a precision that is at least comparable to prior art systems.

To attain these objects, the present invention employs a computer controlled fluorometer and optical train which can measure a plurality of diverse fluorescence and phosphorescence emission properties including lifetimes. The entire instrument including both the nanosecond lifetime, steady state fluorescence and phosphorescence, and phosphorescence lifetime modes of operation will be described in detail hereinafter. When measuring fluorescence and phosphorescence lifetimes, a sample is first excited by a stoboscopically pulsed light source. Sample emissions are used to illuminate a gated detector that has an output that is gated into discrete time windows the positions of which are located in time with respect to the exciting light pulses. The integrated intensity of the signal within each window is determined and recorded The entire emission decay intensity is determined by locating the detection window across the decay profile. The noise statistics required for data analysis are collected simultaneously with each data point. Repeated scans are averaged together to improve the signal to noise ratio and to provide acquisition of data from weakly emitting particles. Data analysis is performed in the computer by a non-linear least squares analysis procedure. The data analysis results are presented for interpretation on computer output and display devices.

The exact nature of this invention as well as other objects and advantages thereof will be readily apparent from consideration of the following specification related to the annexed drawings in which:

DETAILED DESCRIPTION OF THE PREFERRED EMBODIMENT

Figure 1:
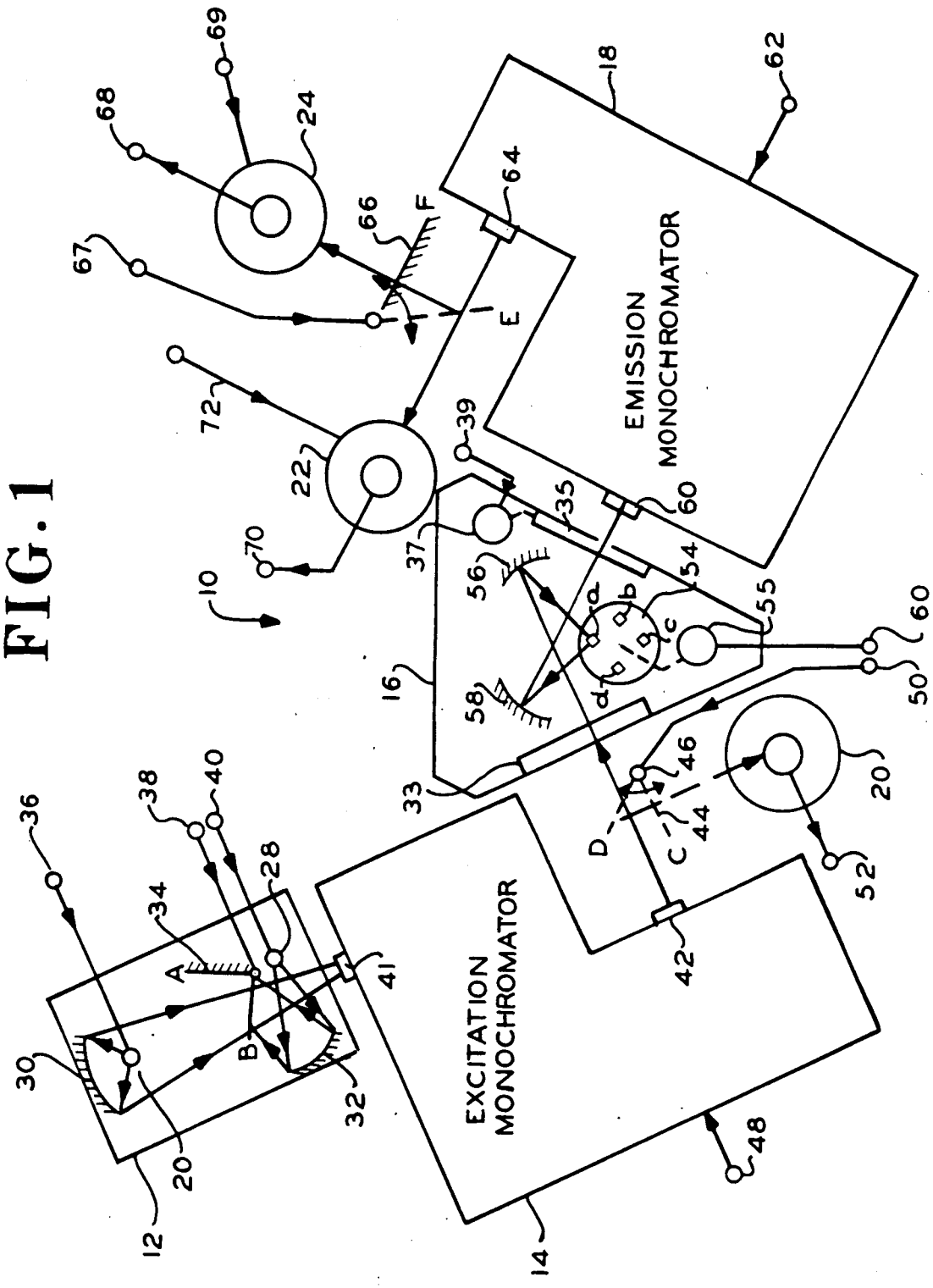
FIG. 1 shows a schematic view of a portion of the preferred embodiment of the present invention.

Referring now to the drawings, wherein like reference characters designate like or corresponding parts throughout the several views, there is shown in FIC 1 a schematic representation of an optical system 10 including a light source 12, an excitation monochromator 14, a sample chamber 16, an emission monochromator 18, and photodetectors 20, 22, 24.

Light source 12 includes a nanosecond lamp 26 and a pulsed xenon lamp 28. Alternatively the light source can be a flash lamp, or a high intensity lamp, or a laser.

A first focusing mirror 30 is mounted with respect to lamp 26 to focus and direct a light beam from lamp 26 to the input 41 of excitation monochromator 14. Light source 12 further includes a second focusing mirror 32 and a pivoted planar mirror 34 that are mounted with respect to lamp 28 to focus and direct a light beam from lamp 28 to the input 41 of excitation monochromator 14. The mirror 34 is pivotably mounted for rotation into either of two positions A or B. When in position A, the mirror 34 is withdrawn to an inactive position to permit the focused light beam from mirror 30 to pass to the input 41 of excitation monochromator 14. When in position B (dashed line), the mirror 34 is aligned with the focused light beam from mirror 32 to direct it to the input 41 of monochromator 14. Input lines 36, 40, 38 are connected to lamp 26, lamp 28 and mirror 34, respectively, to permit input signals to be applied thereto to operate these elements in a manner to be described below. For the present it is sufficient to note that light source 12 selectively focuses light energy at the input 41 of monochromator 14 from either lamp 26 or lamp 28.

The excitation monochromator 14 is a scannable monochromator for selectively providing at output 42 an output light beam at a particular narrow band of wavelengths. A beam splitter 44, mounted adjacent to output 42, has a pivot means 46 for selectively rotating beam splitter 44 between positions C and D. When in position D, the beam splitter 44 transmits a portion of the output beam to the input of sample chamber 16 and reflects a portion to the photodetector 20. When in position C (dashed line), the beam splitter 44 is inactive thereby permitting the output beam from output 42 to be transmitted to the input of sample chamber 16. A pair of input lines 48, 50 are connected to the monochromator 15 and the pivot means 46' respectively. Input line 48 is provided to permit a scanning signal to be applied to monochromator 14 to select which particular narrow band of wavelengths is to be provided at output 42. Line 50 is connected to the pivot means 46 such that a control signal can selectively move splitter 44 between positions C and D. An output line 52 is connected to the output of photodetector 20. Photodetector 20 is preferably a photomultiplier tube (pMT).

The sample chamber 16 includes a sample turret 54 having four sample holders a, b, c, d. A four-position stepper motor 55 is coupled to turret 54 to selectively position turret 54 in one of four positions such that an input stroboscopic light beam focused by an excitation mirror 56 may be directed at one of the four sample holders a, b, c, d. Light emissions from the exposed sample holder (holder "a" in FIG. 1) are focused and directed by a collection mirror 58 to the input 60 of emission monochromator 18. It is noted that the collection mirror 58 is arranged to collect emissions that are directed at an angle, preferably 90°, to the excitation beam from excitation mirror 56. A manually adjustable excitation polarizer 33 is mounted at the input to chamber 16 to permit selective manual adjustment of the polarization of the input light beam. A second emission polarizer 35 is mounted at the output to chamber 16 to permit automatic adjustment of the polarization of the input beam to input 60. A stepper motor 37, having a control input line 39, is provided to permit adjustment of the position of emission polarizer 35. The polarizers 33, 35 are required only when the properties of polarized light are needed to perform certain measurements. The polarizers 33, 35 are not needed for the functioning of the nanosecond lifetime made of operation.

Emission monochromator 18 is a scannable monochromator having a scanning signal input line 62. Light appearing at the input 60 will be resolved by monochromator 18 into a plurality of narrow bands of light energy. A particular one of these bands, as selected by the scanning input signal on line 62, will be transmitted from output 64. The output beam from output 64 may be reflected by pivotable mirror 66 to the photodetector 24. This situation is represented in FIG. 1 by the dashed line designated position E. When in position F, the mirror 66 is inactive and the output beam from output 64 is permitted to pass to photodetector 22. An input line 67 is connected to mirror 66 to provide a control signal for selectively moving mirror 66 between positions E and F. Detectors 24, 22, have output lines 68, 70, respectively. Detector 22 has an input line 72 for gating the detector 22 in a manner to be described below. Photodetectors 22, 24 are also preferably photomultiplier tubes (pMT). pMT 24 is gated by input line 69.

Figure 2:
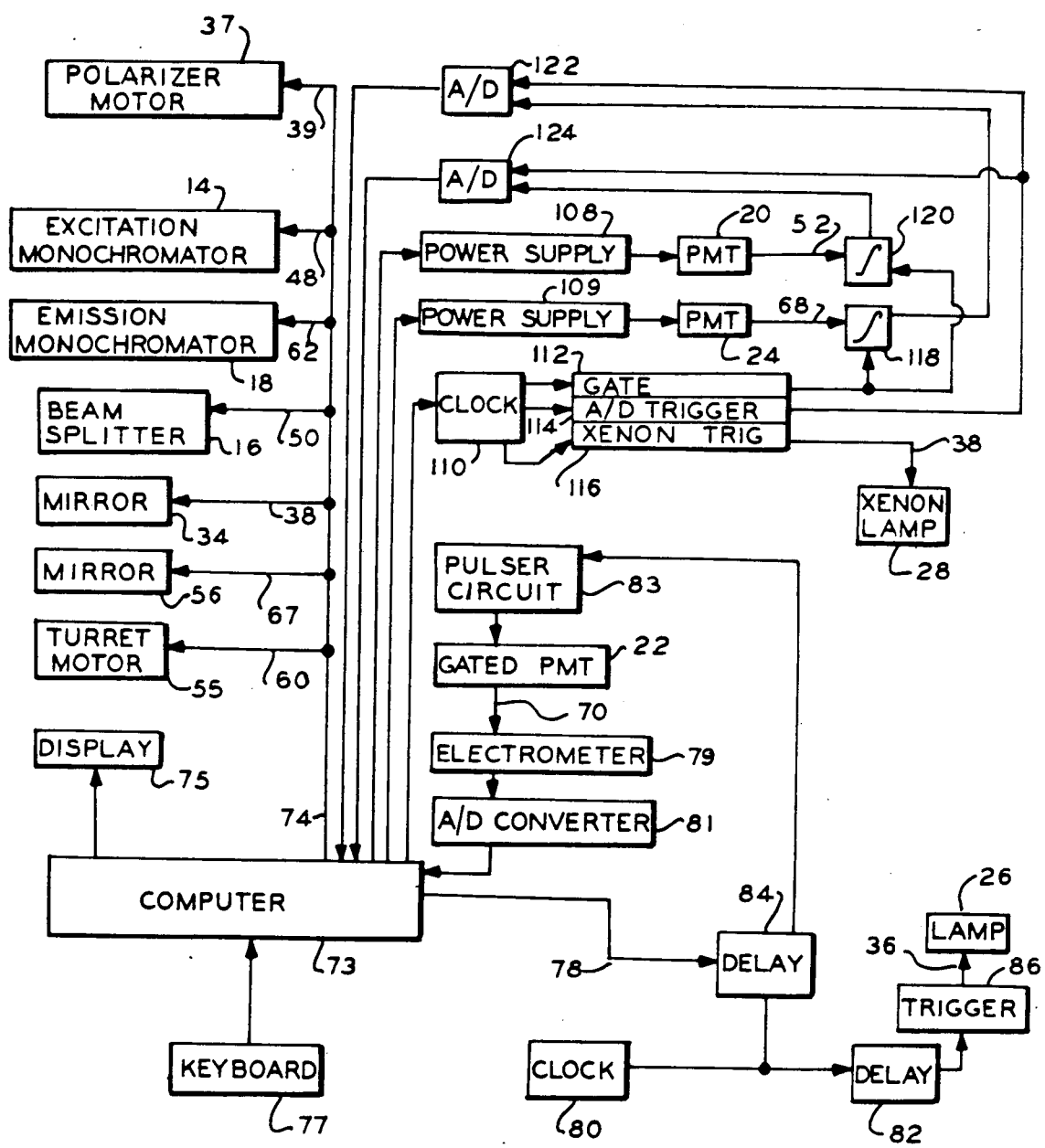
FIG. 2 is a block diagram of the preferred embodiment.

FIG. 2 represents a block diagram of the luminescence system A computer 73 has a plurality of output lines, represented here by bus 74, connected to the control input lines 60, 67, 38, 50, 62, 48, 39, of turret motor 55, mirror 66, mirror 34, beam splitter 46, scannable monochromators 18, 14 and polarizer motor 37, respectively. Computer 73 has an output device, display 75, and an input device, keyboard 77. The output of photodetector 22 is converted into a digital data signal by electrometer 79 and analog to digital converter (A/D converter) 81 for input to computer 73.

DETAILED DESCRIPTION OF THE NANOSECOND DETECTION CIRCUITRY AND NANOSECOND LAMP

The nanosecond detector circuitry comprises a clock 80, typically an external oscillator, which has an output connected to the input of a fixed delay 82 and a variable delay 84. Computer 73 has a delay control output line 78 connected to the control terminal of the variable delay 84 for controlling the delay thereof The output, a delayed clock signal, of delay 84 triggers a high-voltage pulser circuit 83 for providing a high-voltage gate to photodetector 22. Circuit 83 may include an avalanche transistor chain to generate a high-voltage pulse. Delay 82, having a fixed delay, is connected to the input of a nanosecond lamp trigger 86 which in turn is connected to nanosecond lamp 26 via input line 36. Typically, the nanosecond lamp 26 is a gas spark-gap discharge lamp, such as a hydrogen or nitrogen lamp, that is capable of generating a light pulse having a pulse duration of the order of a few nanoseconds. The trigger 86 may be a thyratron tube that is capable of switching the high lamp voltage in response to the low voltage clock pulses of the output of delay 82.

Figure 3:
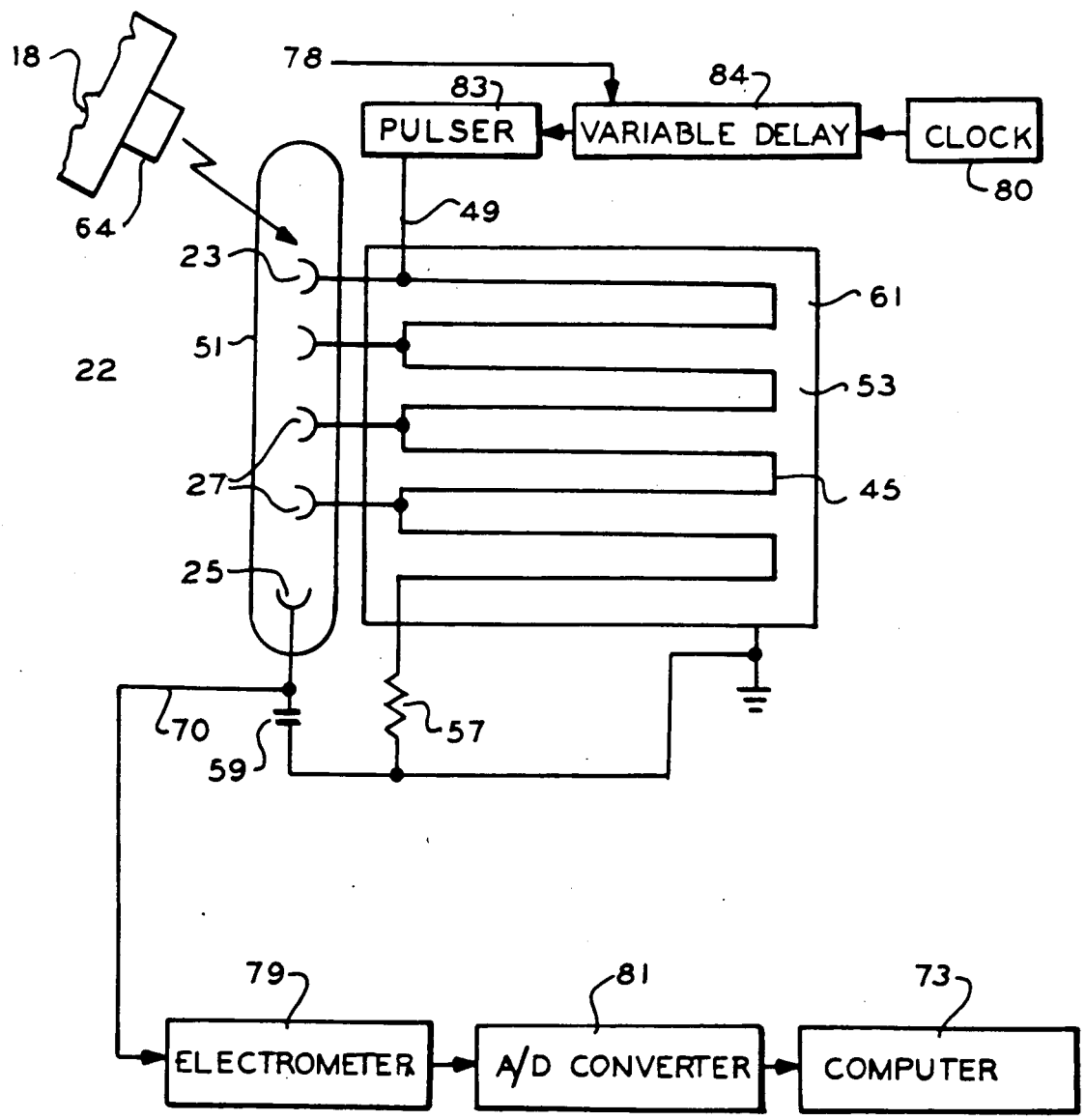
FIG. 3 is a schematic diagram of a portion of the apparatus.

FIG. 3 shows details of the gated photodetector 22 including a conventional tube 51 having a photocathode 23, an anode 25 and a plurality of spaced dynodes 27 connected to a strip-line delay pointed on a circuit board 53 having a ground plane 61. The input 49 of circuit 53 is connected to the photocathode 23 and the output of delay 84. The dynodes 27 are connected to spaced points along a strip line 45 that is mounted above ground plane 61. The delay circuit 53 is terminated in a matching resistor 57 having one side grounded. The anode 25 is connected to ground through a capacitor 59 and to output line 70.

When a clock pulse appears at input 49, it will propagate along the strip line 45. The strip line 45 is designed so that the transit time for an input pulse to travel between the input 49 and each of the successive points connected to the dynodes 27 is equal to the interdynode transit time required for the electrons. In the present invention the use of a pMT, as the photodetector 22, in combination with the dynodes 27, serves the purpose of gating the dynodes in synchronism with the electron transit time. For example, the transit time for electrons to travel from the photocathode 23 to the first dynode 27 will be equal to the time required for a clock pulse to travel from input 49 lo the point at which the first dynode 27 is connected to strip line 45. As such, a clock pulse on strip line 45 will cause amplification of electrons between adjacent dynodes 27 over short time periods that will occur synchronously with the transit of electrons between adjacent dynodes 27 such that the amplifications will be cumulative thereby resulting in a high overall gain over a narrow period called a window. The width of this window, being primarily a function of the shape of the clock pulse plus the strip-line, can be made significantly narrow. Therefore, the output on line 70 of PMT 22 will be zero, except during those short periods when the amplified electron beam reaches anode 25. The value or intensity of the output signal on line 70 will be a function of the intensity of the photoemission taking place from photocathode 23 at the time the clock pulse appears at the input 49 of delay line 45. The intensity of the photoemission, of course, is a function of the instantaneous intensity of the light beam transmitted by output 64. Therefore, in effect, the clock pulses act as gating pulses from photodetector 22, establishing the precise time at which the photodetector 22 provides an output signal The time difference between the generation of a clock pulse by clock 80 and the occurrence of a corresponding amplified output signal on line 70 may be accurately adjusted by varying the input signal on line 78 to variable delay 84.

The system as just described is capable of performing a fluorescence lifetime decay test. As such, the operation of the system with respect to lifetime measurements will now be described:

When a lifetime measurement test is to be run on a sample, the user will first place the sample in one of the sample holders a, b, c, d. The user then inputs the computer 73, via keyboard 77, with appropriate information as to the particular sample holder containing the sample and the type of test lifetime measurement to be conducted. It is noted that although the description is directed to a situation in which a single test is conducted on a single sample, the present invention contemplates that a plurality of tests and test types may be readily conducted on a plurality of samples in response to a single set of computer inputs by the user via keyboard 77. For the present description, it is assumed that only one sample is placed in a sample holder, viz holder "a", and that only one lifetime measurement test is to be conducted.

Figure 4:
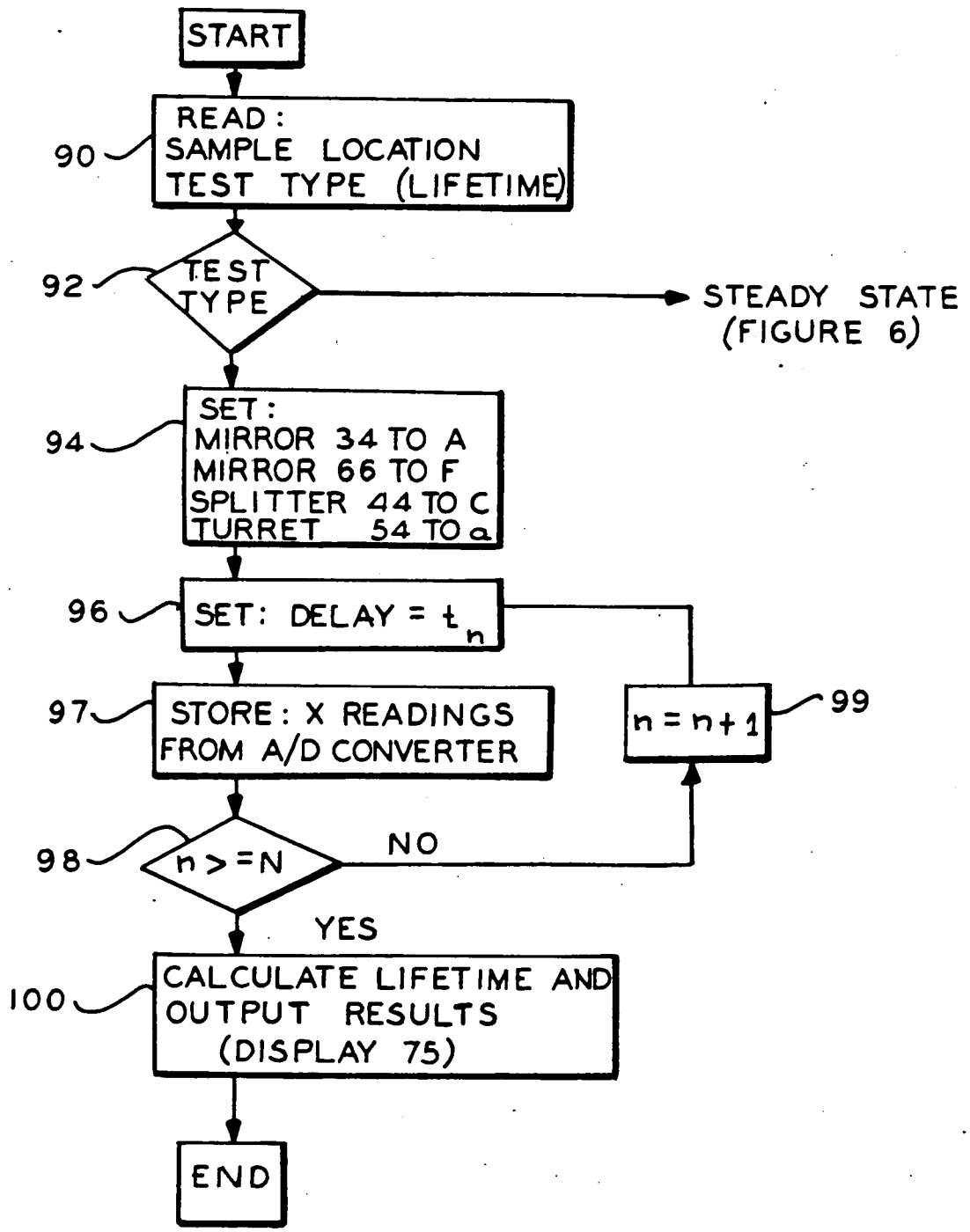
FIG. 4 is a computer flow diagram showing the operation of a portion of the apparatus.

After inputting the initial data, the operator causes the computer 73 to run the procedure detailed in the FIG. 4 flow diagram. As a first step 90, the computer 73 reads the sample location and the requested test type inputted by the operator. As indicated in parenthesis in step 90, the lifetime test is to be conducted on a sample in holder "a". Next, step 92, the computer 73 decides which of two paths to follow based on the test type. In the present example, the operation proceeds along the lifetime path to step 94 wherein the computer 73 sends control signals on bus 74 so that the mirrors 34, 66 are set in positions A, F, respectively, beam splitter 44 is set in position C' and turret 54 is rotated to properly position holder "a" via motor 55. Additionally, in step 94 an index "n" is set equal to 1. In step 96, the computer 73 sends a control signal on line 78 to Variable delay 84 to set the delay thereof equal to a value designated here as $t_1$ since cumulative index "n" at this point is set equal to 1.

Also at this point, the clock 80 is running and a plurality of clock pulses are continuously being sent to trigger 86 to fire nanosecond lamp 26, causing a series of short light pulses to be directed to excitation monochromator 14. Monochromator 14, having been tuned to a particular band of wavelengths by computer 73, will direct a beam of light to sample holder "a" via mirror 56. Mirror 58 will collect fluorescent light emissions from sample holder "a" and focus them at the input 60 of previously tuned monochromator 18. The output 64 of monochromator 18 will then focus its output on the photocathode 23 of the photodetector 22.

The output of variable delay 84 will gate photodetector 22 via circuit 83 at a predetermined time $t_n$ such that an amplified signal, directly related to the emission intensity of the sample in holder "a" appears on the output line 70. The signal on line 70, after conversion to a digital data signal via electrometer 79 and A/D converter 81, is stored in computer 73 As indicated in step 97 (FIG. a number X of such readings are read and stored by computer 73. After X readings have been stored the computer 73, step 98, compares the value of the index "n" with respect to a predetermined value N which represents the arbitrary number of cycles over which data will be collected, typically 10 to 1000. If "n" is not greater than N, the index "n" is incremented in step 99 and the delay $t_n$ is changed to a new value. At this point, the computer 73 changes the delay of variable delay 84 step 96 and stores a new set of X readings from the A/D converter 81, step 97. This cycle is repeated until N sets of readings, with each set including X readings, are stored in computer 73.

After data collection is completed, the computer 73 proceeds to step 100 wherein the lifetime profile of the sample in holder "a" is calculated and outputted either on the display 75 or otherwise, on a plotter or similar device.

Figure 5:
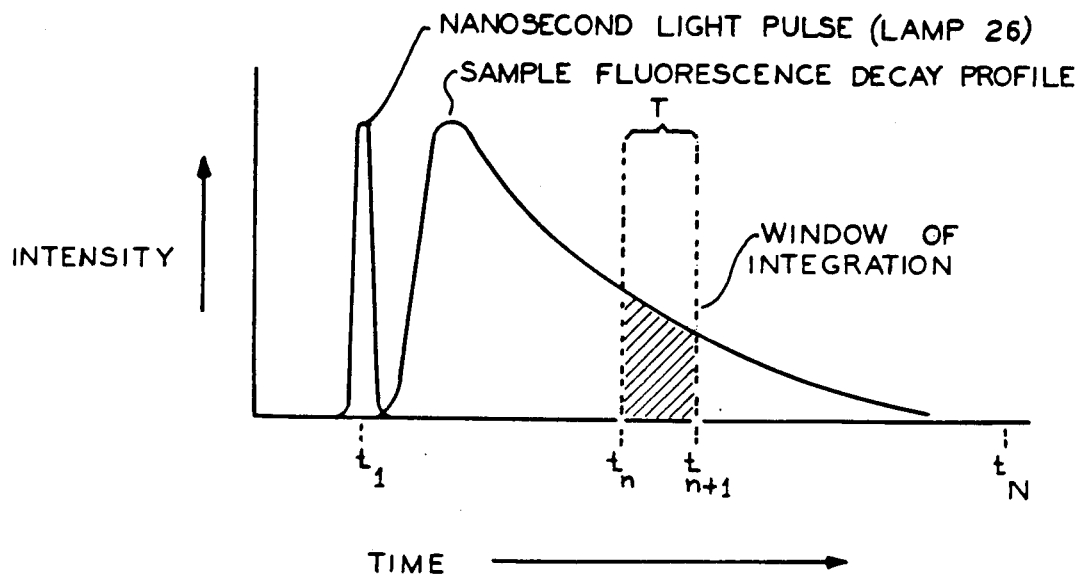
FIGS. 5 is a waveform useful in understanding the operation.

The fundamental scheme under which the above-described system measures fluorescence lifetime decay is analogous to a boxcar integration technique whereby a signal is measured With particular reference to FIG. 5 wherein a single cycle is illustrated, the sample in holder "a" is excited with successive, spaced nanosecond light pulses from lamp 26 to produce sample emissions having a sample fluorescence decay profile which is detected by the gated photodetector 22. The photodetector 22 is gated (FIG. 3) by the variable delay 84 into discrete time windows T, the position of which are located accurately at any time position $t_n$ referenced to the exciting pulse of light. The output of photodetector 22 will represent the integrated intensity of the sample emission over the window T and is represented by the cross-hatched area in FIG. 5 for a window occuring at time $t_n$. The width of window T, a function of the shape of the clock pulses at input 49, is in the order of a few nanoseconds or less.

As such, the entire fluorescence decay profile is determined by computer 73 by systematically locating the detection time window T across the fluorescence decay profile (FIG. 5) to extend from $t_1$ to $t_N$. The noise statistics required for data analysis by computer 73 are collected simultaneously with each data point by storing a plurality X of readings for each window T. Averaging together the X readings allows for improved signal to noise and the acquisition of data from weakly emitting samples.

It is implicit in FIG. 5 that the delay times $t_n$ are contiguous as the index "n" is incremented from 1 to N It is pointed out, however, that it is contemplated that the computer can be readily programmed to produce other types of delay schemes. For instance, widely spaced noncontiguous delay times and pseudorandomly located delay times $t_n$, generating either spaced or overlapping windows T, are also contemplated.

It is also noted that the time spent for data acquisition at any delay time $t_n$ is controllable by computer 73. An almost instantaneous change to a new (step 97), the duration of which is variable and under control of the computer 73 by simply varying the number of readings X. In the application of this feature, multiple readings X of the A/D converter 81 are primarily performed at a given delay time $t_n$ for the purpose of signal enhancement by averaging. In a similar way, data of different amplitudes can be collected to the error limit by using variable collection times.

It is also contemplated that time intervals may be introduced between each delay time tn in order to increase the time range without increasing either the number of data points collected or the time required for data acquisition. The purpose of this feature is to utilize the entire dynamic range of the delay 84 and collect a fixed number of data points at a constant rate of data collection.

Also contemplated in the present invention is the application of baseline subtraction. In this mode of operation, an intensity datum at a given delay time $t_n$ is collected and then the delay 84 is instructed to move to a predetermined "baseline" time position. A baseline datum is collected and is subtrated from the intensity datum. This mode of operation may be used to remove the baseline "dark" current from the observed data as the fluorescence decay is collected. Dark current is the detector response in the absence of light. This procedure is useful because it prevents the accumulation of any systematic drifts in the detection circuitry.

Another contemplated scheme of operation is the use of pseudorandom delay times $t_n$ that are neither contiguous nor do they occur in a linear time sweep Rather, the data are collected at a series of pseudorandomly located positions which eventually monitor the entire time range of interest, each time delay position $t_n$ accessed only once to prevent overcounting. This procedure can be used to randomize systematic, relatively short time drifts in the data collection circuitry and lamp intensity. The effect is simply to spread the drift out over the entire fluorescence decay curve (FIG. 5) as "noise" rather than having the drift occur as an anomoly over a few contiguous data windows T.

In many cases, it is desirable to collect data very quickly but of lower precision, e.g. a snap shot collecting only a few points across the fluorescence decay curve (FIG. 5). This is readily implemented with the delay 84 by setting only a few delays of and noncontiguously jumping from one to the other.

Data enhancement with the use of signal averaging is also contemplated in the present invention. In the simplist case, repeated data acquisitions are simply added together. The average signal to noise ratio improves by the square root of the number of repetitions. This procedure is readily implemented with the delay 84 by virtue of its ability to rapidly and exactly reposition the window T to any desired time position. A new datum is collected and added to the previous datum from this time position resulting in signal averaging. It is essential that the exact time position is accessed otherwise there will be an erroneous averaging of more than just one time position.

In addition to lifetime profile analysis, the present invention can also be used to perform steady state fluorescence tests. Steady state fluorescence tests performable with the present invention are the determination of fluorescence and phosphorescence spectra and the determination of phosphorescence decay lifetimes.

Returning to FIG. 2, computer 73 is shown as having a pair of control outputs connected to controllable power supplies 108, 109 for adjusting the gain of pMTs 20. 24, respectively. The output lines 52, 68 of pMTs 20, 24 are connected to the inputs of resetable integrators 118, 120, respectively. Computer 73 also has an output connected to a clock 110 having three phased clock outputs connected to gate 112, A/D trigger 114 and xenon trigger 116. The output of gate 112 is connected to the reset inputs of resetable integrators 118, 120. The outputs of integrators 118, 120 are connected to two data inputs of computer 73 via triggered A/D converters 122, 124, respectively. The A/D converters 122, 124 are triggered by outputs from the A/D trigger 114. The xenon lamp 28 is triggered synchronously with clock 110 by the xenon trigger 116 via line 38.

Figure 7:
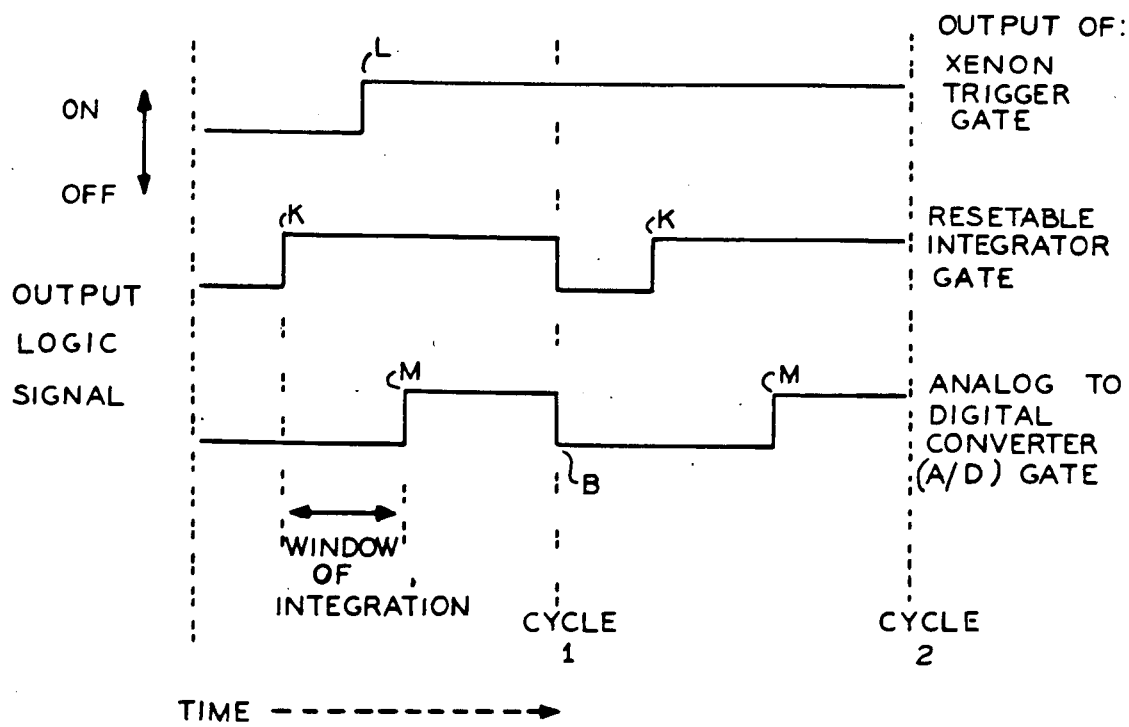
FIG. 7 is a timing diagram useful in understanding the principles of the present invention.
Figure 6:
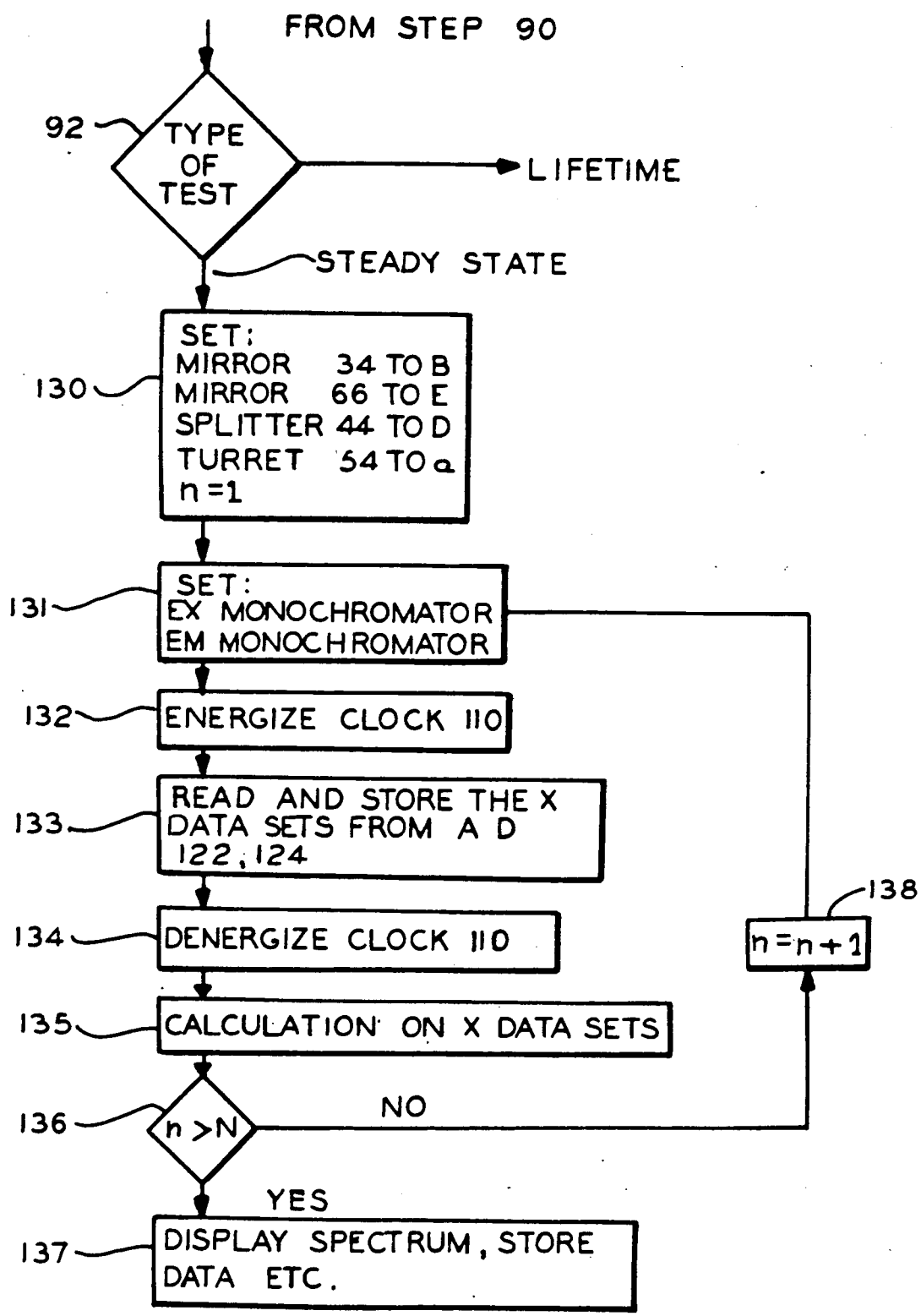
FIG. 6 is a computer flow diagram showing the operation of a portion of the apparatus.

With particular reference to FIGS. 6, 7, the operation of this portion of the system is shown with respect to the performance of a steady state test. In a steady state test a sample is placed in the sample holder, the operator runs the instrument 10 from the computer 73, the sample is illuminated from lamp 28, the light impressions are collected, and the intensity of the emissions are determined from the gated photodetector 24. When the computer 73 detects a request for a steady state test, step 92, it proceeds to step 130 wherein mirrors 34, 66 are set in position B, E, respectively, beam splitter 44 is made operative and moved to position D, and the turret 54 is moved to properly position the sample holder "a". In step 131, the monochromators 14 and 18 are set to the appropriate value. Next, in step 132, the clock 110 is energized by computer 73 causing three sets of phased clock pulses to be outputted by clock 110. The timing diagram of FIG. 7 shows the first and second cycles of the system after the clock 110 is energized.

As shown in FIGS. 2, 6, 7, first the integrators 118, 120 are reset by the output of gate 112 (point K, FIG. 7). Next, the xenon lamp 28 is flashed (point L) and then the A/D converters 122, 124 are triggered ON by A/D trigger 114 (point M) collecting data point number 1. In the subsequent cycle, the xenon lamp remains OFF while the output of the A/D trigger 114 turns OFF (point B). The integrators 118, 120 are reset (point B) and again turned ON (point K). Further, after a short period of time, the A/D converters 122, 124 are triggered by A/D trigger 114 (point M) collecting data point number 2. During the first of these cycles, the light from the xenon lamp 28 is directed at the sample in holder "a."

It is again noted that because beam splitter 44 is made active by rotation to position D, a portion of the light beam being directed to sample holder "a" is reflected to photodetector 20. The output of photodetector 20 is used as a reference. Further, because mirror 66 has been rotated to position E, the output beam from output 64 is reflected to pMT 24. The gated photodetector 22 is not used during a steady slate test From the time that the integrators 118, 120 are gated ON (point K) they integrate the outputs of photodetector 24, 20, a measure of the cumulative intensity at the optical outputs 64, 42 of monochromators 18, 14, respectively. After a predetermined integration period, referred to in FIG. 7 as the "window-of-integration" time, the A/D converters 122, 124 are triggered to convert the outputs of integrators 118, 120 into digital data signals for storage in computer 73.

The two above cycles will be repeated. After a predetermined number, X, of these cycles during which X data sets have been stored (step 133) in computer 73, the clock 110 is deenergized (step 134).

In step 135, the X data sets consisting of point number 1 and point number 2 may then be used to calculate the sample emission intensity For example, point number 2 may be subtracted from point number 1 to correct for background signal levels. All the X points, whether corrected in this manner or not, may be averaged together to improve the signal to noise ratio. The output values from pMT 20 may be used to correct the emission intensity values for lamp intensity variations. The results of the test are then presented to display 75 by the computer 73.

Referring to FIG. 6, in step 136 the program determines if the test is done. If it is, the date acquisition stops and the spectrum is displayed in step 137. If the test continues, the program counter 138, is incremented and the monochromators are moved to the next wavelength and the data acquisition cycle 132 to 135 is repeated.

It will be understood that the present invention is not limited to the structure or components disclosed hereinabove by way of example.

The scope of the present invention is limited only by the appended claims

What is claimed is:

1. An integrated luminescence-measuring system for selectively conducting lifetime decay or steady-state measurements of fluorescent or phosphorescent light emitted by a sample when the sample receives excitation light, wherein the system comprises:

(A) chamber means containing a plurality of samples for directing excitation light received therein at a selected sample, and for directing fluorescent or phosphorescent light emitted by the selected sample to the exterior thereof;

(B) first monochromator means for for transmitting excitation light which comprises selected wavelengths and which is derived from the input light into the chamber means;

(C) second monochromator means for for producing output light which comprises selected wavelengths and which is derived from the emitted light;

(D) illumination module means which includes a plurality of sources of focused light for transmitting such light to the first monochromator means;

(E) a gated photodetector having a gating input and an output, signals directly related to the intensity of received light appearing on the output if a signal is also present on the gating input;

(F) a first photodetector having an output on which signals appear which are directly related to the intensity of received light;

(G) means for selectively directing the output light from the second monochromator means to the gated photodetector or the first photodetector;

(H) reference module means, which includes
 (i) a second photodetector having an output on which signals appear which are directly related to the intensity of received light, and
 (ii) means for directing the excitation light to the chamber means or for directing some of the excitation light to both the second photoconductor and the chamber means;

(I) a first detector subsystem, which includes
 (i) a first normally deenergized source of first serial pulses,
 (ii) means for delaying the first pulses by a fixed amount and for pulsatingly energizing a selected light source in response thereto,
 (iii) means for selectively delaying the first pulses by a variable amount and for applying the variably delayed pulses to the gating input of the gated photodetector, and
 (iv) first convertor means which receives signals on the output of the gated photoconductor and for producing digital signals related thereto, the digital signals produced by the first convertor means occurring a selected time after light pulses from the selected light source, being directly related to the intensity of the output light at such selected time, and representing the integral of such intensity taken over the time-width of the variably delayed pulses;

(J) a second detector subsystem which includes
 (i) a second normally deenergized source of second serial pulses,
 (ii) means for pulsatingly energizing a selected light source in response to the second pulses,
 (iii) resetable integrator means connected to the outputs of the first and second photodetectors,
 (iv) means for resetting the integrators in response to second pulses,
 (v) normally "off" analog-to-digital convertor means for receiving from the integrator means analog signals representing the time integrals of the signals on the outputs of the first and second photodetectors and for producing digital signals, respectively representative thereof,
 (vi) means for gating "on" the analog-to-digital convertor means in response to second pulses, and
 (vii) means for adjusting the phase relationship among the second pulses received by the selected light source, the integrator resetting means, and the convertor gating "on" means, so that respective outputs of the second and analog-to-digital convertor means carry signals representative of the respective time integrals, taken during an integration window of selected widths, of signals on the respective outputs of the first and second photodetectors; and (K) digital data processing means
 (i) for selecting a sample for receipt of excitation light, for selecting the wavelengths of the excitation light and the output light, for selectively energizing a selected pulse source, selectively directing the output light to the gated photodetector or to the first photoconductor and, if the latter, to direct excitation light to the second photodetector, (ii) if the gated photoconductor receives output light and if the first pulse source is energized, for varying the delay of the first pulses by differing amounts so that a selected number of integrals of the intensity of the output light are taken over varying time-widths, and for storing digital signals from the analog-to-digital convertor means representing a selected number of integrals over each such time-width, and (iii) if the first and second photoconductors receive light and if the second pulse source is energized, for storing a selected number of digital signals from the second and third analog-to-digital convertor means representative of the time integrations performed by the integrator means and using the integration of the second photodetector output as a reference for the integration of the first photodetector output.

2. An integrated luminescence measuring system for selectively conducting lifetime decay or steady state measurement of fluorescent or phosphorescent light emitted by a sample at a test site when the sample receives excitation light, wherein the system comprises:

(A) A chamber surrounding the test site which holds a plurality of samples and which includes means for directing excitation light received in the chamber to the test site and for directing fluorescent or phosphorescent light emitted by a sample at the test site to the exterior of the chamber;

(B) a first adjustable monochromator for receiving input light and for transmitting excitation light to the chamber, the excitation light being derived from and including selected wavelengths of the input light;

(C) a second adjustable monochromator for receiving emitted light from the chamber and for producing output light, the output light being derived from and including selected wavelengths of the emitted light;

(D) an illumination module which includes
  (i) a plurality of selectively energizable sources of pulsed, focused light, and
  (ii) means for permitting the focused, pulsed light from a selected source to be received as input light by the first monochromator;

(E) a gated photodetector having a gating input for receiving output light from the second monochromator, the gated photodetector producing an output directly related to the intensity of received output light when a signal is present on the gating input;

(F) a first photodetector for receiving output light from the second monochromator, the photodetector producing an output directly related to the intensity of the received output light;

(G) adjustable means for selectively directing the output light from the second monochromator to the gated photodetector or to the first photodetector;

(H) a reference module, which includes
  (i) a second photodetector which produces an output directly related to the intensity of excitation light incident on the second photodetector, and
  (ii) adjustable means for selectively
    (a) permitting all of the excitation light to reach the chamber and for permitting none of the excitation light to reach the second photodetector, or
    (b) directing excitation light to the second photoconductor and to the chamber;

(I) a first detector subsystem, which includes
  (i) a first selectively energizable source of serial pulses,
  (ii) means for delaying pulses from the first source by a fixed amount and for energizing and pulsing one of the light sources in response thereto,
  (iii) means for selectively delaying pulses from the first source by a variable amount and for applying the variably delayed pulses to the gating input of the gated photodetector,
  (iv) first convertor means for receiving the output of the gated photoconductor and for producing digital signals representative thereof, whereby the digital signals produced by the first convertor means occur a selected time after the occurrence of the light pulses from the one light source, are directly related to the intensity of the output light at such selected time, and represent the integral of such intensity taken over the time-width of the variably delayed pulses on the gating input;

(J) a second detector subsystem which includes
  (i) a second selectively energizable source of pulses,
  (ii) means for energizing and pulsing another of the light sources in response to pulses from the second pulse source,
  (iii) a first resetable integrator which receives the output of the first photodetector,
  (iv) a second resetable integrator which receives the output of the second photodetector,
  (v) means for resetting the integrators in response to pulses from the second pulse source,
  (vi) normally "off" analog-to-digital convertors for respectively receiving from the integrators analog signals representing the time integral of the signals on the outputs of the first and second photodetectors and for producing digital signals representative thereof,
  (vii) means for gating "on" the convertors in response to pulses from the second pulse source, and
  (viii) means for adjusting the phase relationship among the pulses received from the second pulse source by the other light source, the integrator resetting means, and the convertor gating "on" means, so that the convertors produce signals representative of the respective time integrals, taken during integration windows of selected widths, of the respective outputs of the first and second photodetectors; and (K) digital data processing means
  (i) for presenting a selected sample at the test site,
  (ii) for adjusting the monochromators so that the excitation light and the output light, respectively, comprise selected wavelengths,
  (iii) for selectively energizing one of the pulse sources to energize one of the light sources, to permit light from the selected light source to be received by the first monochromator, to adjust the output-light-directing means, and to selectively adjust the excitation-light-permitting means,
  (iv) if the gated photoconductor receives output light and if the first clock is energized, for affecting the variable delaying means to selectively vary the delay of the pulses from the first clock by differing amounts so that a selected number of integrals of the intensity of the output light are taken over varying the time widths, and for storing digital signals from the first convertor representing a selected number of integrals over each such time-width, and (v) if the first photoconductor receives output light, if the second clock is energized, and if the second photoconductor receives excitation light, for storing a selected number of digital signals from the second and third analog-to-digital convertors representative of the time integrations performed by the integrators and using the integration of the second photodetector output as a reference for the integration of the first photodetector output.

3. An integrated luminescence-measuring system for selectively conducting lifetime decay or steady-state measurement of fluorescent or phosphorescent light emitted by a sample at a test site when the sample receives excitation light, wherein the system comprises:

(A) A sample chamber, which includes
  (i) a rotatable turret,
  (ii) a plurality of sample holders on the turret, which holders are selectively locatable at the test site upon rotation of the turret,
  (iii) means for rotating the turret,
  (iv) first means for directing excitation light received in the chamber to the test site, and
  (v) second means for directing fluorescent or phosphorescent light emitted by a sample at the test site to the exterior of the chamber;

(B) a first monochromator for receiving input light and for transmitting excitation light, which is derived from the input light, to the first directing means, the first monochromator including means for selectively permitting the output excitation light to comprise selected wavelengths of the input light;

(C) a second monochromator for receiving emitted light from the second directing means and for producing output light which is derived from the emitted light, the second monochromator including means for selectively permitting the output light to comprise selected wavelengths of the emitted light;

(D) an illumination module, which module includes
  (i) first and second pulsable, selectively energizable sources of light,
  (ii) means for focusing light issuing from each source, and
  (iii) multipositionable means for, depending on the position thereof, permitting the focused light from the first or the second light source to be received as input light by the first monochromator;

(E) a gated photodetector for receiving output light from the second monochromator, the gated photodetector including a gating input and an electrical output, there appearing on such output, when a signal is present on the gating input, an electrical signal directly related to the intensity of the received output light;

(F) a first photodetector for receiving output light from the second monochromator, the first photodetector including an electrical output on which there appear electrical signals directly related to the intensity of the received output light;

(G) means for selectively directing the output light from the second monochromator to the gated photodetector or to the first photodetector;

(H) a lifetime measurement reference module, which includes
  (i) a second photodetector having an electrical output on which there appear electrical signals directly related to the intensity of light incident on the second photodetector, and
  (ii) selectively positionable means for
    (a) in a first position, permitting all of the excitation light to reach the first directing means and permitting none of the excitation light to reach the second photodetector, and
    (b) in a second position, directing some of the excitation light to the second photoconductor and to the first directing means;

(I) a first detector subsystem, which includes
  (i) a first, selectively energizable clock for producing serial pulses,
  (ii) means for delaying pulses from the first clock by a fixed amount and for energizing and pulsing the first light source in response thereto,
  (iii) means for selectively delaying pulses from the first clock by a variable amount and for applying the variably delayed pulses to the gating input of the gated photodetector,
  (iv) a first analog-to-digital convertor for receiving the electrical signals on the output of the gated photoconductor and for producing digital signals related thereto, whereby the digital signals produced by the first convertor occur a selected time after the occurrence of the light pulses from the first light source, are directly related to the intensity of the output light at such selected time, and represent the integral of such intensity taken over the time-width of he delayed pulses on the gating input;

(J) a second detector subsystem which includes
  (i) a second selectively energizable clock for producing serial pulses,
  (ii) means for energizing and pulsing the second light source in response to pulses from the second clock
  (iii) a first resetable integrator connected to the output of the first photodetector,
  (iv) a second resetable integrator connected to the output of the second photodetector,
  (v) means for resetting the integrators in response to pulses form the second clock,
  (vi) a normally "off" second analog-to-digital convertor for receiving from the first integratory analog signals representing the time integral of the signals on the output of the first photodetector and for producing digital signals representative thereof on an output,
  (vii) a normally "off" third analog-to-digital convertor for receiving from the second integrator analog signals representing the time integral of the signals on the output of the second photodetector and for producing digital signals representative thereof on an output,
  (viii) means for gating "on" the second and third analog-to-digital convertors in response to pulses from the second clock, and (ix) means for adjusting the phase relationship among the pulses received from the second clock by the second light source, the integrator resetting means, and the convertor gating "on" means, so that respective outputs of the second and third analog-to-digital convertors carry signals representative of the respective time integrals, taken during an integration window of selected widths, of signals on the respective outputs of the first and second photodetectors; and (K) digital data processing means
  (i) for selectively rotating the turret to locate a selected sample holder at the test site,
  (ii) for selectively affecting the monochromators so that the output excitation light and output light, respectively, comprise selected wavelengths,
  (iii) for selectively energizing one of the clocks to energize one of the light sources, to selectively position the multipositionable permitting means, to selectively adjust the selective output-light-directing means, and to selectively position the excitation-light-related selectively positionable means,
  (iv) if the gated photoconductor receives output light and if the first clock is energized, for affecting the variable delaying means to selectively vary the delay of the pulses from the first clock by differing amounts so that a selected number of integrals of the intensity of the output light are taken over varying time-widths, and for storing digital signals from the first analog-to-digital convertor representing a selected number of integrals over each such time-width, and
  (v) if the first photoconductor receives output light, if the second clock is energized, and if the second photoconductor receives excitation light, for storing a selected number of digital signals from the second and third analog-to-digital convertors representative of the time integrations performed by the integrators and using the integration of the second photodetector output as a reference for the integration of the first photodetector output.

* * * * *